United States Patent [19]

Wang et al.

[11] Patent Number: 5,679,680

[45] Date of Patent: Oct. 21, 1997

[54] α-SUBSTITUTED HYDRAZIDES HAVING CALPAIN INHIBITORY ACTIVITY

[75] Inventors: Kevin Ka-Wang Wang, Ypsilanti; Po-Wai Yuen, Ann Arbor, both of Mich.

[73] Assignee: Warner-Lambert Company, Morris Plains, N.J.

[21] Appl. No.: 389,525

[22] Filed: Feb. 16, 1995

[51] Int. Cl.$^6$ .................. A61K 31/495; C07D 241/54
[52] U.S. Cl. ............... 514/249; 544/354; 564/434
[58] Field of Search ..................... 544/354; 514/249

[56] References Cited

U.S. PATENT DOCUMENTS

| | | | |
|---|---|---|---|
| 4,124,718 | 11/1978 | Giroux et al. | 514/427 |
| 4,169,149 | 9/1979 | Giroux et al. | 514/428 |
| 4,347,255 | 8/1982 | Giroux | 514/461 |
| 4,400,382 | 8/1983 | Brown et al. | 544/354 |
| 4,439,443 | 3/1984 | Giroux | 514/438 |
| 4,999,436 | 3/1991 | Witzel et al. | 549/45 |

FOREIGN PATENT DOCUMENTS

| | | |
|---|---|---|
| 040401A1 | 11/1981 | European Pat. Off. . |
| 603769A1 | 6/1994 | European Pat. Off. . |
| 603873A1 | 6/1994 | European Pat. Off. . |
| 282006A | 4/1983 | German Dem. Rep. . |
| 7193474 | 5/1981 | Japan . |
| 60-166641 | 8/1985 | Japan . |
| 7305766 | 2/1975 | South Africa . |
| 9306103 | 4/1993 | WIPO . |
| 94/21639 | 9/1994 | WIPO . |

OTHER PUBLICATIONS

Brorson et al, *J. Neurosci.* 14, pp. 187–197 (1994).
Shearer et al, *Opthalmol. Vis. Sci.* 32, pp. 533–540 (1991).
Rami et al, *Brain Res.* 609, pp. 67–70 (1993).
Arlinghaus et al, *Europ. J. Pharmacol.* 209, pp. 123–125 (1991).
K.K-W. Wang, et al., *TiPS*, 1994, 15:412–419.
S-C. Hong, et al., *Stroke*, 1994, 25:3, 663–669.
R.T. Bartus, et al., *J Cerebral Blood Flow & Metab*, 1994, 14:537–544.
H. Caner, et al., *Brain Research*, 1993, 607:354–356.
T.C. Saido, et al., *J of Biological Chemistry*, 1992, 267:34, 24585–24590.
T. Murachi, *Biochem Intl*, 1989, 18:263–294.
K. Wang, *TiPS*, 1990, 11:139–142.
B. Meldrum, et al., *TiPS*, Special Report: 1991, 54–92.
R. Siman, et al., *J Neurosci*, 1989, 9:5, 1579–1590.
A. Arai, et al., *Brain Research*, 1990, 532:63–68.
D. Holtzman, et al., *TIBS 16*, 1991, 140–144.
N. Iwamoto, et al., *Brain Research*, 1991, 561:177–180.
R. Siman, et al, *J Neurosci*, 1990, 10:7, 2400–2411.
T.R. Shearer, et al., *Current Eye Research*, 1987, 6:2, 289–300.
J.M. Marcantonio, et al., *Biochemical Society Translations*, 1991, 19:1148–1150.
M. Azuma, et al., *Current Eye Research*, 1991, 10:7, 657–666.
N.L. Banik, et al., *Central Nervous System Trauma*, 1984, 1:2, 131–137.
W.C. Taft, et al., *Soc Neurosciences Abs*, 1991, 17:65.8.
N. Banik, et al., *J Neurochemistry*, 1985, 45:2, 581–588.
K. Iizuka, et al., *Biochemical Medicine & Metabolic Biology*, 1991, 46:427–431.
G. Toda, et al., *Jpn Heart J*, 1989, 30:3, 375–386.
W. McBride, et al., *New England J of Medicine*, 1988, 318:1734–1737.
K.L. March, et al., *Clinical Research*, 1990, 38:2, 234A.
R.L. Wilensky, et al., *JACC*, 1991, 17:2, 268A.
I. Fukui, et al., *Biochem & Biophy Res Comm*, 1989, 162:2, 559–566.
K. Suzuki, et al., *Biochem J*, 1992, 285:857–862.
H. Sugita, et al., *Calcium Regulation in Biological Systems*, 1984, ed. S. Ebashi, 243–256.
P. Johnson, et al., *Int J Biochem*, 1988, 20:11, 1227–1230.
R.N. Puri, *American J Physiol*, 1990, 259: C862.
J.J. Baldassare, et al., *J Biological Chem*, 1985, 260:19, 10531–10535.
R.N. Puri, et al., *Blood*, 1991, 77:3, 500–507.
B.L. Sharma, et al., *J. Applied Tox*, 1986, 6:4, 253–257.
J. Wagner, et al., *Can J Chem*, 1977, 55:4028–4036.
T.H. Haskell, et al., *J Med Chem*, 1970, 13:4, 697–704.

*Primary Examiner*—Emily Bernhardt
*Attorney, Agent, or Firm*—Elizabeth M. Anderson

ABSTRACT

The invention covers a novel series of α-substituted hydrazides that inhibit both calpain I and calpain II. They are non-peptide irreversible active site inhibitors of calpain. The compounds are useful in the treatment of neurodegenerative disorders including cerebrovascular disorders, brain injury, spinal cord, and peripheral nerve injury, cardiac infarction, cataracts, inflammation, restenosis, muscular dystrophy, and platelet aggregation. Pharmaceutical compositions, methods of using processes for preparing and novel intermediates useful in the processes are also disclosed.

6 Claims, No Drawings

α-SUBSTITUTED HYDRAZIDES HAVING CALPAIN INHIBITORY ACTIVITY

BACKGROUND OF THE INVENTION

Calcium-dependent protease (calpain) exists in most mammalian cell types. This enzyme has two major isoforms that differ in their sensitivity to calcium ions (calpain I and calpain II) (see Murachi T, *Biochem Int* 1989;18: 263–294). Calpain resides in the cytosol of cells and is activated by $Ca^{2+}$ at physiological pH. Its proteolytic activity appears to be selective against certain target proteins, such as components of the cytoskeleton and calmodulin-dependent enzymes. To date, there are no high affinity, selective, nonpeptide inhibitors of calpain reported (see Wang K K W, *Trends Pharmacol Sci* 1990;11: 139–142).

Excessive excitation by a neurotransmitter glutamate can lead to death of nerve cells (neurons) and neurodegeneration (see Meldrum B, Garthwaite J, *Trends Pharmacol Sci*, Special Report 1991, 1991: 54–62. It is believed that toxic effect of glutamate comes from overactivation of its target glutamate receptors (e.g., under ischemic conditions or stroke). This in turn produces an influx of calcium ion ($Ca^{2+}$) into the neurons. The rise of cellular $Ca^{2+}$ level triggers the activation of calpain. Calpain then goes on to degrade cytoskeletal protein such as spectrin, which is believed to disrupt normal cellular functions, and eventually leads to cell death (Siman R, Noszek J C, Kegerise C, *J Neurosciences* 1989;9: 1579–1590). Inhibition of calpain by products covered by the present invention minimizes the cellular damage and therefore prevents neurodegeneration. Several nonselective calpain inhibitors were shown to be neuroprotective in various ischemia models (Arai A, Kessler M, Lee K S, Lynch G, *Brain Res* 1990;532: 63–68).

Abnormal protein processing is implicated in Alzheimer's disease and calpain and several of its target proteins including the amyloid precursor protein and tau protein have been identified as major components of Alzheimer's neurofibrillary tangles (Holtzman D M, Mobley W C, *Trends Biochem Sci* 1991;16: 140–144; Iwamoto N, Thangnipon W, Crawford C, Emson P C, *Brain Res* 1991: 177–180) in affected regions of the brain. Amyloid precursor protein has also been found to be sensitive to calpain digestion (Siman R, et al., *J Neuroscience* 1990;10: 2400–2411). It is conceivable that calpain activity may be defective that leads to abnormal processing of its target protein. It argues that inhibition of calpain by products covered in the present invention will provide therapeutical benefits to the patients of Alzheimer's disease.

Cataract is an opacity occurring in the lens as a result of a variety of insults to the lens (Shearer T R, David L L, Anderson R S, *Current Eye Res* 1987;6: 289–300). In an experimental model where cataract is induced by overdose of sodium selenite (selenite cataract), it has been shown that the lens shows increase of calcium and water-insoluble proteins. Calpain is also found in high concentration in corneal lens epithelium. In selenite cataract, it was demonstrated that lens proteins such as α-, β-crystallins, and cytoskeletal proteins were degraded during cataract formation. (Marcantonio J M, Duncan G, *Biochem Soc Trans* 1991;19: 1148–1150). Cysteine protease inhibitor E64, which inhibits calpain, has been shown to reduce the rate of cataract formation in whole animal (Azuma M, David L L, Shearer T R, *Current Eye Res* 1991;10: 657–666). Calpain inhibitors such as the compounds covered in the present invention can be of use in retarding cataract formation.

It has been demonstrated that intracellular calcium level rises after traumatic injury to brain or spinal cord (Banik N L, Hogan E L, Whetstine L J, Balentine J D, 1984;1: 131–137). Overactivation of calpain is supposed to play a role on the degenerative process that occurs after the injury, similar to the excitatory amino acid toxicity in the brain (Taft W C, Lyeth B G, Dixon C E, Hayes R L, *Soc Neurosciences* 1991: 164, Abstr. 17). There is also evidence of calpain degradation of myelin protein which can cause neurodegeneration (Banik N, McAlhaney W W, Hogan E L, *J Neurochemistry* 1985;45: 581–588). Calpain inhibitors of the present invention can minimize the degeneration observed.

Ischemic myocardiac infraction is a result of blockade of blood supply in the coronary Vessels. It has been reported that calpain activation was observed in the cardiac myocytes during these conditions (Iizuka K, Kawaguchi H, Yasuda H, *Biochemical Medicine and Metabolic Biology* 1991;46: 427–431) coronary reperfusion of cysteine protease inhibitor E64c after acute myocardiac infraction in dogs was found to significantly reduce the size of infract (Toda G, Matsushita S, Kuramoto K, et al., *Jap Heart J* 1989;30: 375–386). Again, calpain inhibitors in the present invention can provide therapeutic benefits.

Percutaneous transluminal coronary angioplasty is now a widely accepted medical procedure to expand the inner diameter of clotted artery in atherosclerotic coronary artery disease patients. However, the success rate of this procedure is dampened by the spontaneous, slow renarrowing of the arteries (restenosis) (McBride W, Lange R A, Hillis L D, *New Eng J Med* 1988;318: 1734–1737). Recently, it has been shown that controlling proliferation and migration of smooth muscle cells to the neoinitimal layer of the blood vessel by calpain inhibitor I and other cysteine protease inhibitors (March K L, Roeske R, Hathaway D R, Olin Res 1990;38: 234A). It was further shown that these agents can inhibit restenosis (Wilensky R L, March K L, Hathaway D R, *J Amer Coll Cardiol* 991;17: 268A). Since the compounds in this invention are also calpain inhibitors, they should be useful in reducing angloplastic restenosis.

Calpain is found in the synovial (joint) fluid of the knee joint. In fact, both calpain I and II in the synovial fluid were found to increase by several-fold in rheumatoid arthritis patients (Fukui I, Tanaka K, Murachi T, *Biochem Biophys Res Commun* 1989;162: 559–566). A major cartilage component proteoglycan was also found to be a calpain substrate (Suzuki K, et al., *Biochem J* 1992;285: 857–862). It is believed that calpain overactivation has a damaging effect of the joint and in the inflammation process itself. Inhibition of calpain activity by compound in the present instant invention may provide therapeutic benefit to the patients suffering from such inflammation.

Disruption in the regulation of intracellular calcium concentration was reported in muscular dystrophy, such as Duchenne muscular dystrophy (DMD) and after muscle denervation. Intracellular calcium levels in muscular dystrophic mice was found to be significantly raised which resulted in increased protein degradation. Many myofibrillar proteins (such as myosin, Troponin I and T) are indeed good calpain substrates (Sugita H, Ishiura S, Kamakura K, Nakase H, Hagiwara K, Nonaka I, In: *Calcium Regulation in Biological Systems*, (Ebashi S, Endo M, Imahori K, Kakiuchi S, Nishizuka Y, eds, Academic Press, 1984: 243–257.) and calpain II concentration was higher in dystrophic skeletal muscle in animals (Johnson P, Hammer J L, *Int J Biochem* 1988;20: 1227–30). Therefore, it is conceivable that calpain overactivation plays an important role in abnormal myofiber degradation. Calpain inhibitors described in this invention will be useful treatment in muscular degenerative disorders such as muscular dystrophy or muscle denervation.

Formation of blood clots (thrombosis) is a result of platelet aggregation. When platelets are stimulated by thrombin or plasmin, two key events occur which lead to platelet aggregation (Puri R N, et al., *Am J Physiol* 1990;259:C862): 1) putative ADP-receptor aggregin is proteolyzed and 2) fibrinogen receptors become exposed on the platelet surface. Aggregin was hydrolyzed in vitro by calpain but not by thrombin. It was further found that thrombin increased intracellular calcium levels in platelets thus activating calpain which then hydrolyzed aggregin. Calpain also appeared to modify platelet membrane structure thus exposing latent fibrinogen receptor (Baldassare J J, et al., *J Biol Chem* 1985;260: 10531–10535). This allows fibrinogen binding to platelet that leads to aggregation. It was shown that calpain inhibitors Phe-Gln-Val-Val-Cys(3-nitro-2-thiopyridine)-Gly-$NH_2$ and high molecular weight kininogen blocked aggregin breakdown and platelet aggregation (Purl R N, et al., *Am J Physiol* 1990;259:C862; Puri R N, et al., *Blood* 1991;77: 500–507). Therefore, calpain inhibitors described in this patent should be effective platelet aggregation inhibitors.

Increasing evidence suggests that excessive activation of the $Ca^2$-dependent protease calpain could play a role in a variety of disorders: cerebral ischemia cataracts, myocardial ischemia, muscular dystrophy, and platelet aggregation (Wang, K K W, et al., *TIPS* 1994;15: 412–419).

Results demonstrate the neuroprotective effect of a cell-penetrating calpain inhibitor when administered systemically and therefore targeting intracellular, calcium-activated mechanisms such as proteolysis is a viable therapeutic strategy for limiting neurological damage after ischemia (Hong S-C, et al., *Stroke* 1994;25: 663–669).

A series of studies demonstrates that a potent calpain inhibitor, AK275, applied directly to the surfaces of ischemic neocortex can dramatically and unequivocally reduce the size of the expected infarct (Bartus R T, et al., *J Cereb Blood Flow Metab* 1994;14: 537–577).

Copending United States application Ser. No. 08/132,624 filed May 21, 1993, now U.S. Pat. No. 5,534,767 teaches a series of α-mercaptoacrylic acids as having potent calpain inhibitory activity. This is hereby incorporated by reference.

SUMMARY OF THE INVENTION

The present invention is a series of substituted hydrazides of Formula

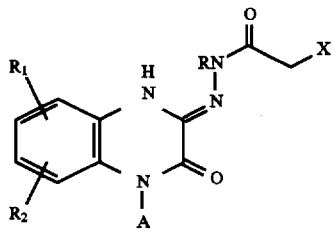

the tautomers or isomers thereof and the pharmaceutically acceptable base or acid addition salt thereof wherein R, $R_1$, $R_2$, A, and X are as described below.

These selective nonpeptides inhibit both calpain I and calpain II and are irreversible active site inhibitors.

The present invention also includes pharmaceutical compositions comprising therapeutically effective amount of one or more of a compound of Formula I together with a pharmaceutically acceptable carrier in unit dosage form.

The present invention includes methods of using the compounds of Formula I in the treatment of neurodegenerative disorders including cerebrovascular disorders as well as in the treatment of traumatic brain injury, spinal cord and/or peripheral nerve injury, cardiac infraction, cataract, inflammation, restenosis, muscular dystrophy, and platelet aggregation.

The present invention also includes a method of treating disorders responsive to the blockade of one or both of calpain I and calpain II comprising administering to a mammal, including a human, in need thereof a therapeutically effective amount of the above composition.

The invention also includes treating stroke, cerebral ischemia, cerebral infarction, cerebral vasospasm, hypoglycemia, cardiac arrest, Alzheimer's disease, traumatic brain injury, spinal cord and/or peripheral nerve injury, cardiac infraction, cataract, inflammation, restenosis, muscular dystrophy, and platelet aggregation.

The invention further includes processes for the preparation of compounds of Formula I.

The invention still further includes novel intermediates useful in the processes.

DETAILED DESCRIPTION OF THE INVENTION

The compounds of the instant invention are selective nonpeptide inhibitors of calpain.

The α-substituted hydrazides of the instant invention are those of Formula

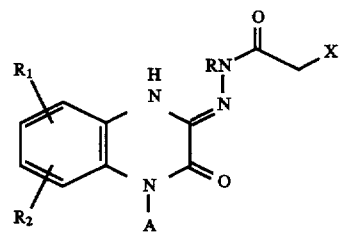

the tautomers and isomers thereof and a pharmaceutically acceptable salt thereof wherein A is alkyl or

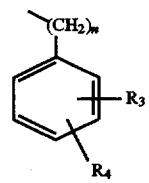

where n is an integer of from 0 to 3;

$R_1$ and $R_3$ are each independently hydrogen, alkyl, alkenyl, alkynyl, aryl, heteroaryl, arylalkyl, arylalkenyl, arylalkynyl, heteroarylalkyl, heteroarylalkenyl, and heteroarylalkynyl;

$R_2$ and $R_4$ are each independently hydrogen,
halogen,
hydroxy,
alkyl,
alkoxy,
amino,
nitro,
cyano, and
COOR$_5$ wherein R$_5$ is hydrogen, alkyl, or aryl;
R is hydrogen,
alkyl, or
aryl; and
X is halogen,
alkoxy, or
O$_2$CR$_6$ wherein R$_6$ is hydrogen, alkyl, or aryl.

Preferred compounds of the invention are those of Formula I wherein

R$_1$ and R$_3$ are each independently hydrogen;

R$_2$ and R$_4$ are each independently selected from hydrogen, halogen, hydroxy, and COOR$_5$ wherein R$_5$ is hydrogen, alkyl, or aryl;

R is hydrogen or alkyl; and

X is halogen or O$_2$CR$_6$ wherein R$_6$ is hydrogen, alkyl, or aryl.

More preferred compounds of the invention are those of Formula I wherein

R, R$_1$, and R$_2$ are each hydrogen;

A is methyl, phenyl, or 4-chlorophenyl; and

X is chloro or bromo.

The most preferred compounds of the invention are those of Formula I and selected from 2-chloro-acetic acid (4-methyl-3-oxo-3,4-dihydro-1H-quinoxalin-2-ylidene)-hydrazide;

2-bromo-acetic acid (3-oxo-4-phenyl-3,4-dihydro-1H-quinoxalin-2-ylidene)-hydrazide;

2-chloro-acetic acid [4-(4-chloro-phenyl)-3-oxo-3,4-dihydro-1H-quinoxalin-2-ylidene]-hydrazide; and 2-chloro-acetic acid (3-oxo-4-phenyl-3,4-dihydro-1H-quinoxalin-2-ylidene)-hydrazide.

The alkyl groups contemplated in the instant invention such as alkyl per se, aminoalkyl, arylalkyl, heterocycloalkyl are both straight and branched carbon claims.

Lower alkyl means a straight chained or branched chain of from one to six carbon atoms including but not limited to methyl, ethyl, propyl, n-propyl, butyl, 2-butyl, isobutyl, pentyl, hexyl, n-hexyl, and the like. The alkyl groups may be unsubstituted or substituted by one or more selected from: halogen, hydroxy, amino, and alkoxy.

Alkenyl means a group from two to six carbon atoms, containing at least one double bond. These are, for example, but not limited to ethylene, 1,2- or 2,3-propylene, 1,2-, 2,3-, or 3,4-butylene, 1,2-, 2,3-, 3,4- or 4,5-pentylene, or hexylene, or isomers thereof.

Alkynyl means a group from two to about six carbon atoms, containing at least one triple bond. These are, for example, but not limited to ethynyl, 2,3-propynyl or 3,4-butynyl, or isomers thereof.

Cycloalkyl means a saturated ring of from three to about six or seven carbon atoms. Such groups included but are not limited to cyclopropyl, cyclobutyl, cyclopentyl, cyclohexyl which are unsubstituted or substituted by one or more selected from: halogen, alkoxy, alkyl, or hydroxy.

Cycloalkenyl means an unsaturated ring of from four to six carbon atoms containing one or two carbon-carbon double bond(s).

Heterocycle means a 5- or 6-membered monocyclic, bicyclic, or tricyclic group, containing at least one to as many as four heteroatoms in one ring if monocyclic or at least one of the rings, if fused bicyclic or tricyclic. Heteroatoms are nitrogen, oxygen, or sulfur or a combination thereof, where possible. Such heterocycles include, thienyl, benzothienyl, furanyl, benzofuranyl, pyrazinyl, pyrazolyl, pyridazinyl, pyridyl, pyrimidinyl, pyrrolyl, isothiazolyl, thiazolyl, oxazolyl, isoxazolyl, triazolyl, tetrazolyl, imidazolyl, thiadiazolyl, benzothiadiazolyl, oxadiazolyl, benzothiazolyl, indolyl, carbazolyl, quinolinyl, isoquinolinyl, or N-oxides thereof.

The term aryl includes substituted or unsubstituted phenyl, naphthyl, and biphenyl. The substituents include one or more selected from: halogen, nitro, alkyl, alkoxy, alkylthio, hydroxy, or others as specified.

The term halogen includes fluorine, chlorine, bromine, and iodine.

Well known protecting groups and their introduction and removal may be used according to the skill in the art and are described, for example, in McOmie J F W, *Protective Group in Organic Chemistry*, Plenum Press, London, New York (1973) and Greene T W, Wuts P G M, *Protective Groups in Organic Synthesis*, Second Edition, Wiley, New York (1991).

The compounds of the present invention may contain asymmetric carbon atoms. The instant invention may also include the individual diastereomers and enantiomers, which may be prepared or isolated by methods known to those skilled in the art.

Selected compounds of the present invention can exist also as syn and anti forms and are also claimed in the present invention. Selected compounds can also exist as E and Z double bond isomers. Both forms are included in the present invention.

The compounds of the present invention can also exist in tautomeric forms.

Any resulting racemate can be resolved into the optical antipodes by known methods, for example by separation of the diastereomeric salts thereof, with an optically active amine, and liberating the optically active acid compound by treatment with an acid. Racemic compounds of the present invention can thus be resolved into their optical antipodes e.g., by fractional crystallization of d- or 1-α-methylbenzylamine, brucine, quinidine, or quinine salts.

Additional methods for resolving optical isomers, known to those skilled in the art may be used, for example those discussed by J. Jaques, A. Collet, and S. Wilen in *Enantiomers, Racemates, and Resolutions*, John Wiley and Sons, New York (1981).

Pharmaceutically acceptable salts of the compounds of Formula I are also included as a part of the present invention.

The base salts may be generated from compounds of Formula I with one equivalent of a suitable nontoxic, pharmaceutically acceptable base followed by evaporation of the solvent employed from the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well-known to practitioners of the pharmaceutical formulation arts. See, for example, Berge S N, et al., *J Pharm Sci* 1977;66: 1–19.

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well-known in the art.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

The compounds of the present invention can be administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which my also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethyl-cellulose, a low-melting wax, cocoa butter, and the like. The term "preparation" is intended to include the formulation of the active compound with encapsulating material as a carrier providing a capsule in which the active component, with or without carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low-melting wax, such as a mixture of fat glycerides or cocoa butter, is first melted and the active component is dispersed homogeneously therein, as by stirring. The molten homogeneous mixture is then poured into convenient-sized molds, allowed to cool, and thereby to solidify.

Liquid form preparations include solutions, suspension, and emulsions, for example, water or water propylene glycol solutions. For example, parenteral injection liquid preparations can be formulated in solution, such as, in aqueous polyethylene glycol solution.

Aqueous solutions suitable for oral use can be prepared by dissolving the active component in water and adding suitable colorants, flavors, stabilizing, and thickening agents, as desired.

Aqueous suspensions suitably for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg preferably 10 mg to 100 mg according to the particular application and the potency of the active component. The composition can, if desired, also contain other compatible therapeutic agents.

The compounds of the instant invention exhibit valuable pharmacological properties by selectively inhibiting the calcium-dependent neutral proteases in mammals. The compounds are thus useful for treating diseases responsive to calcium-dependent neutral proteases inhibition in mammals.

Such disorders include but are not limited to cerebral ischemia or cerebral infarction resulting from a range of conditions such as thromboembolic or hemorrhagic stroke, cerebral vasospasm, hypoglycemia, cardiac arrest, status epilepticus, and perinatal asphyxia, anoxia such as from drowning, pulmonary surgery, and cerebral trauma. Other treatments are for neurodegenerative disorders such as Alzheimer's disease, spinal cord and/or peripheral nerve injury, and poisoning by exogenous NMDA poisons (e.g., some forms of lathyrism). Further uses include treatment for cardiac infraction, cataract, inflammation, restenosis, muscular dystrophy, and platelet aggregation.

Specifically, the compounds of the present invention have activity as inhibitors of the calcium-dependent neutral proteases. As such, the compounds of the present invention are calpain-specific cysteine proteinase inhibitors.

For example, compounds of the invention exhibit valuable biological properties because of these calcium-depending neutral proteases inhibiting properties. These properties may be ascertained in one or more of the following assays.

BIOLOGICAL TESTING

EXAMPLE 1

Assay of calpain activity: Calpain I was purified from human erythrocytes as described by Wang K K W, Roufogalis B D, and Villalobo A, *Arch Biochem Biophys* 1988;267: 317–327. Calpain activity was assayed in a 96-well microplate format (Buroker-Kilgore M and Wang K K W, *Anal Bio Chem* 1993;208: 387–392). In 250 µL of reaction mixture, substrate casein (0.5 mg/mL) was incubated with 0.01 unit (80–120 ng) calpain I, 20 mM dithiothreitol (DTT), 50 mM Tris-HCl (pH 7.4 at 25° C.) and 4 mM $CaCl_2$ at 25° C. for 60 minutes. Two 100-µL aliquots were taken for Coomassie blue G250 binding analysis to quantify the remaining casein.

As can be seen from the results of Table I, the α-substituted hydrazides listed showed various potency against calpain I and II in this in vitro assay. Compound concentrations that cause 50% inhibition ($IC_{50}$) are as shown (Table I). The second rate of inactivation of calpain I for 2 compounds are also shown.

TABLE I

Inhibitory Activity of α-Substituted
Hydrazides Against Human Calpain I and II

| Example | $IC_{50}$ (μM) Calpain I | $IC_{50}$ (μM) Calpain II | Ki/[I] ($M_{-1}s_{-1}$) Calpain I |
|---|---|---|---|
| 5 | 0.364 | 0.590 | 109 |
| 4 | 0.697 | 0.574 | ND |
| 9 | 0.486 | 0.158 | 63.7 |
| 14 | 8.28 | 10.84 | ND |

ND = Not determined.

EXAMPLE 2

Selectivity of α-substituted Hydrazides: Calpain I and II were assayed as described in Example 1. One to 2 ng papain (papaya latex, Sigma, P3125), 1.25 μg trypsin (bovine pancreas, Sigma, T8003), 5 μg thermolysin (Bacillus thermoproteolyticus, Sigma, P1512) were assayed using 0.5 mg/mL casein as substrate in the microplate format (250 μL reaction volume), essentially a described by Buroker-Kilgore, M. and Wang K K W, Anal Biochem 1993;208: 387–392. Cathepsin B (0.002 unit, bovine spleen) was assayed with 50 mM MES (pH 5.5), 100 μM carbobenzoxy-Arg-Arg-4-methoxy-beta-naphthlamide (Cbz-Arg-Arg-MNA), inhibitor, and 2 mM DTT in 200 μL for 60 minutes at room temperature. Fifty-microliter aliquots were transferred to a fluorescence-compatible plate and then read with a Perkin-Elmer fluorometer LS-50B (excitation 340 nm and emission 425 nm). Calcineurin (bovine brain, Sigma) (5 μg, 0.8 unit) was assayed with 10 mM p-nitrophenyl phosphate in 1 mM DTT, 1 mM $CaCl_2$, 1 mM $MnCl_2$, 200 μM calmodulin (CaM, if added), and 50 mM Tris-HCl (pH 7.4) at 25° C. for 60 minutes or more. Production of p-nitrophenol was monitored at 405 nm. Inhibition of these proteases are presented as $IC_{50}$.

As shown in Table II, example of α-substituted hydrazides inhibited Calpain I and II with $IC_{50}$ between 0.36 μM to 0.59 μM but did not inhibit trypsin (a serine protease) or metalloprotease thermolysin. Papain (a cysteine protease) was inhibited at higher concentrations. Therefore, these results showed that the α-substituted hydrazides showed good selectivity for calpain over other proteases.

TABLE II

Inhibitory Activity of α-Substituted Hydrazide Example
5 Against Various Proteases

| Protease | $IC_{50}$ (μM) |
|---|---|
| Calpain I | 0.364 |
| Calpain II | 0.590 |
| Cathepsin B | >200 |
| Papain | 5.6 |
| Trypsin | >200 |
| Thermolysin | >500 |
| Calmodulin-calcineurin | >500 |

EXAMPLE 3

Cell-based calpain assay: Previously, it was demonstrated that A23187 treatment of human leukemic Molt-4 cells lead to a distinct spectrin breakdown by endogenous calpain, namely the formation of 150 kD and 145 kD fragments sequentially (Saido, et al., J Biol Chem 1992;267: 24585–24590). In our studies, Molt-4 cells were washed three times with serum-free RPMI 1640 medium and resuspended to 4 million/0.5 mL and transferred to a 12-well plate (0.5 mL/well). Calpain inhibitor was added to the wells if desired and preincubated for 1 hour. To activate endogenous calpain, 15 μM of A23187 (as 5 mM DMF stock) was then added, and the cells were further incubated for 90 minutes at 37° C. The cells were then lysed with 2% (w/v) SDS, 5 mM EGTA, 5 mM EDTA, 150 mM NaCl, 0.5 mM PMSF, 10 μg/mL AEBSF, 5 μg/mL leupeptin, 10 μg/mL pepstatin, 10 μg/mL TLCK, 10 μg/mL TPCK, and 20 mM Tris-HCl (pH 7.4) at room temperature for 5 to 10 minutes. One hundred microliters of 100% (w/v) TCA was added and total protein precipitate was collected by microcentrifugation. The final pellets were neutralized with Tris base. Protein samples (50 μg) were run on SDS-PAGE with the Tris-glycine running buffer system and transferred onto a PVDF membrane. The blots were probed with an anti-spectrin (nonerythroid) antibody and a second antibody with alkaline phosphatase conjugate. The blots were developed with nitro blue tetrazolium and 5-bromo-4-chloro-3-indolyl-phosphate. Pretreatment of cells with α-substituted hydrazides diminished the 145 kD fragment formation with an $IC_{50}$ of 15 to 25 μM (Table III).

TABLE III

Inhibitory Activity of α-Substituted Hydrazides on
Spectrin Breakdown in Human Leukemic Molt-4 cells Treated
With Calcium Ionophore A23187

| Example | $IC_{50}$ (μM) |
|---|---|
| 5 | 25 |
| 4 | 25 |
| 9 | 15 |

EXAMPLE 4

Neuroprotective Effects of α-Substituted
Hydrazides in Cerebrocortical Neuronal Cultures (i) Assay of Lactate dehydrogenase (LDH): Fetal rat cortical cell cultures were grown on 12-well plates as described by Koh J Y, Choi D W, J Neurosci Methods 1987;20: 83–90). Seventeen-day-old cultures were pretreated with 200 μM calpain inhibiting compound (when added) for 1 hour before treatment of 500 μM N-methyl-D-aspartate (NMDA) for 30 minutes (in the absence or the presence of the compound). After an additional 4 hours in the absence or the presence of the compound (Example 5), LDH release from neurons to the medium as a measurement of NMDA-induced cell death was performed similarly as described by Koh J Y, Choi D W, J Neurosci Methods 1987;20: 83–90).

Data shown in Table IV illustrated that 195 minutes of hypoxia/hypoglycemia induced about 170 unit/mL LDH release from the cells. We also found that Example 5 of α-substituted Hydrazides enabled the neurons to resist the oxygen/glucose deprivation for longer, as reflected by the LDH release after 24 hours.

TABLE IV

| Effects of the Compound of Example 5 on Oxygen/Glucose Deprivation Induced LDH Release from Fetal Rat Cerebrocortical Cultures | |
|---|---|
| Conditions | LDH release (Unit/mL) |
| Normoxia | 46.13 ± 6.08 (6) |
| Hypoxia/Hypoglycemia | 143.81 ± 9.72 (6) |
| The compound of Example 5 | 57.27 ± 8.11 (6)** |

The data shown are means and SEM. The number of experiment performed was in brackets.
**Significantly different from Hypoxia/Hypoglycemia alone (p < 0.001).

(ii) Neuroprotective effects of the compound of Example 5 against AMPA toxicity to Purkinje cells in cerebellar Slices: Cerebellar slices were acutely isolated from adult rats and maintained in an oxygenated bath for the duration of the experiment as described elsewhere (Caner, et al., *Brain Research* 1993;607: 354–356). Example 5 (100 µM) was added to the ACSF (124 mM NaCl, 3.3 mM KCl, 2 mM $CaCl_2$, 25.7 mM $NaHCO_3$, 2.4 mM $MgSO_4$, 1.25 mM $KH_2PO_4$, 10 mM glucose) 60 minutes before the addition of amino-3-hydroxy-5-methyl-4-isoxazole propionic acid (AMPA; 30 µM for 30 minutes). The slices were then allowed to recover in normal ACSF for an additional 90 minutes. Histological damage to Purkinje cells was identified and quantified as described in detail elsewhere (Caner, et al., *Brain Research* 1993;607: 354–356).

The data as in Table V showed that AMPA-induced neurotoxicity can be ameliorated with the compound of Example 5.

Together, the above results show the α-substituted hydrazides described above are neuroprotective.

TABLE V

| Neuroprotective Effects of the Compound of Example 5 Against AMPA Toxicity to Purkinje Cells in Cerebellar Slices | |
|---|---|
| Conditions | % Live Purkinje Neurons |
| Control | 94.41 ± 0.97 (10) |
| AMPA | 13.41 ± 2.34 (10) |
| AMPA + the Compound of Example 5 | 51.03 ± 4.80 (10)** |

The data shown are means and SEM. The number of experiment performed was in bracket.
**Significantly different from AMPA treatment alone (p < 0.005.).

Therefore, the compounds of Formula I and their pharmacologically acceptable salts are effective agents in the prophylaxis and/or therapeutic treatment of disorders responsive to agents which inhibit calcium-dependent neutral proteases, thus forming a further aspect of the present invention in like manner.

In view of the data presented the novel compounds of the instant invention are expected to be useful in the treatment of central nervous system disorders related to their biological activity. This includes alleviation, treatment, or elimination of an indication associated with the biological activity. This includes especially calpain-related psychosis, calpain-related anorexia, calpain-related ischemia, stroke, cerebral vasospasm, traumatic brain injury, and spinal cord and/or peripheral nerve injury. It also includes cardiac infarction, cataract, inflammation, restenosis, muscular dystrophy, and platelet aggregation.

The following examples are illustrations of the instant invention but are not intended to limit its scope.

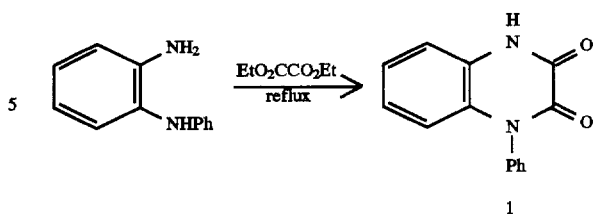

Reference: Cheeseman G W H, *J. Chem. Soc.*, 1804 (1955).

A solution of N-phenyl-o-phenylenediamine (10.79 g, 58.56 mmol) in 25 mL of diethyl oxalate was refluxed for 5 hours. The blue colored suspension was cooled to room temperature and diluted with ethanol (60 mL). The solid was collected and washed with ethanol (2×60 mL). The grey solid was dried in vacuum to give 9.59 g of the quinoxalinedione 1. It was used without further purification.

$^1$HNMR (300 MHz, DMSO-$d_6$) δ12.14 (1H, s), 7.66–7.53 (3H, m), 7.39 (2H, d, J=7.02 Hz), 7.23 (1H, dd, J=7.93, 1.39 Hz), 7.14 (1H, dr, J=8.48, 1.16 Hz), 6.98 (1H, dr, J=8.14, 1.08 Hz), 6.31 (1H, d, J=7.33 Hz).

EXAMPLE 2

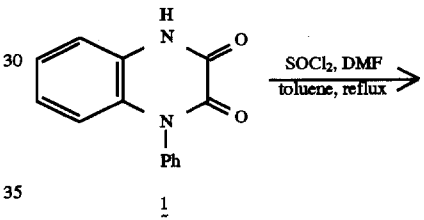

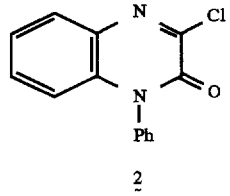

To a suspension of the quinoxalinedione 1 (4.38 g, 18.38 mmol) in toluene (175 mL) and dimethylformamide (11 mL) was added thionyl chloride (2 mL, 27.42 mmol). The grayish suspension was refluxed for 4 hours. At the end of the 4-hour period, the green solution was cooled to room temperature. Water (100 mL) was added and the mixture was stirred at room temperature for 15 minutes. The organic layer was collected and dried with magnesium sulphate, filtered and concentrated. The residue was redissolved in ethyl acetate (250 mL). Active charcoal (3 g) was added and the mixture was heated to reflux. The mixture was filtered hot to remove charcoal. The residue was washed with ethyl acetate (3×60 mL). The filtrate and washings were concentrated to give a solid. The solid was triturated with hot 20% ethyl acetate in hexanes (200 mL). The off-white solid was collected by filtration then air-dried overnight to give 3.50 g of the chloro Compound 2.

$^1$HNMR (300 MHz, DMSO-$d_6$) δ7.84 (1H, dd, J=7.90, 1.46 Hz), 7.70–7.61 (3H, m), 7.50–7.37 (4H, m), 6.56 (1H, dd, J=8.24, 1.22 Hz).

EXAMPLE 3

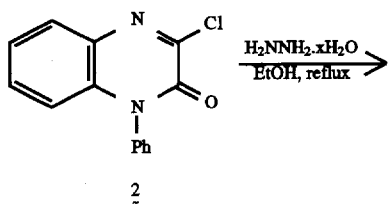

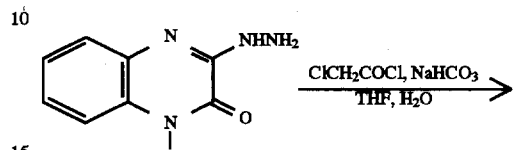

To a suspension of the chloro Compound 2 (1.87 g, 7.29 mmol) in absolute ethanol (20 mL) was added hydrazine hydrate (8.8 mL). The mixture was refluxed for 1 hour. The reaction mixture was cooled to 0° C. and diluted with water (12 mL). The off-white precipitate was collected and washed with water (2×30 mL) then with ether (30 mL). The solid was then air-dried to give 1.68 g of the product.

$^1$HNMR (300 MHz, DMSO-$d_6$) δ8.95 (1H, br s), 7.67–7.58 (3H, m), 7.47 (1H, d, J=7.86 Hz), 7.40 (2H, d, J=7.09 Hz), 7.18 (1H, t, J=7.60 Hz), 7.01 (1H, t, J=7.70 Hz), 6.37 (1H, d, J=8.59 Hz), 4.63 (2H, br s).

EXAMPLE 4

2-Bromo-acetic acid (3-oxo-4-phenyl-3,4-dihydro-1H-quinoxalin-2-ylidene)-hydrazide

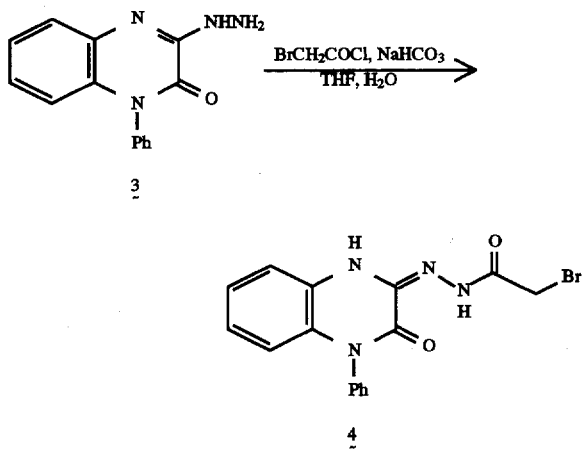

To a solution of the hydrazone 3 (1.06 g, 4.20 mmol) in 100 mL of tetrahydrofuran was added a 1M aqueous solution of sodium bicarbonate (15 mL). Bromoacetyl chloride (0.5 mL, 6.06 mmol) was added slowly into the reaction mixture at room temperature. The mixture was stirred at room temperature for 20 minutes. Water (50 mL) was added and the mixture was saturated with sodium bromide. The organic layer was collected and the aqueous layer was extracted with ethyl acetate (3×50 mL). The combined organic layers was dried with magnesium sulphate, filtered and concentrated to give a 0.94 g of a brown solid. The solid was dissolved in 50 mL of hot methanol, charcoalized, filtered, and cooled to room temperature to give 0.62 g of hydrazide 4 as a white solid; mp=215° C. (dec).

Anal. Calcd for $C_{16}H_{13}BrN_4O_2$: C, 51.49; H, 3.51; N, 15.01. Found: C, 52.27; H, 3.51; N, 15.15.

EXAMPLE 5

2-Chloro-acetic acid (3-oxo-4-phenyl-3,4-dihydro-1H-quinoxalin-2-ylidene)-hydrazide

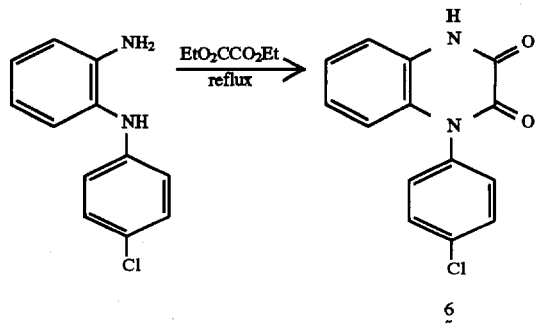

To a solution of the hydrazone 3 (2.38 g, 9.43 mmol) in 200 mL tetrahydrofuran was added 75 mL of a half-saturated sodium bicarbonate solution. The reaction mixture was cooled to 0° C. and chloroacetyl chloride (1 mL, 12.56 mmol) was added slowly. The reaction mixture was stirred at 0° C. for 30 minutes. The mixture was saturated with sodium chloride and the organic layer was collected. The aqueous layer was re-extracted with ethyl acetate (3×100 mL). The combined organic layers was dried with magnesium sulphate, filtered and concentrated to give an off-white solid. The solid was recrystallized in methanol to give 2.45 g of the hydrazide.

$^1$HNMR (400 MHz, DMSO-$d_6$) δ10.41 (1H, br s), 9.55 (1H, br s), 7.63–7.53 (3H, m), 7.48–7.39 (2H, m), 7.17 (1H, t, J=7.57 Hz), 7.07 (1H, t, J=7.69 Hz), 6.38 (1H, d, J=8.06 Hz), 4.21 (2H, s).

EXAMPLE 6

A mixture of 2-amino-4'-chlorodiphenylamine (15.08 g, 68.96 mmol) and diethyl oxalate (27.49 g, 1.88 mol) was refluxed for 4 hours. The purple colored suspension was cooled to room temperature. Ethanol (60 mL) was added.

The solid was collected by filtration and washed with ether (5×60 mL). ¹HNMR (400 MHz, DMSO-d₆) δ12.20 (1H, s), 7.65–7.54 (3H, m), 7.39 (2H, d, J=7.23 Hz), 7.23 (1H, d, J=2.17 Hz), 7.04 (1H, dd, J=8.92, 2.41 Hz), 6.29 (1H, d, J=8.92 Hz).

EXAMPLE 7

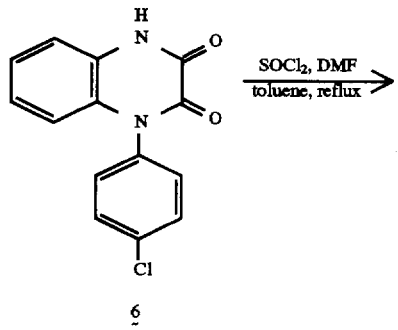

6

To a suspension of the quinoxalinedione 6 (8.89 g, 32.60 mmol) in 360 mL of toluene was added 23 mL of dimethylformamide and thionyl chloride (5 mL, 68.55 mmol). The suspension was refluxed for 4 hours. The deep blue solution was cooled to room temperature. Water (200 mL) was added and the mixture was stirred at room temperature for 10 minutes. The organic layer was collected and the aqueous layer was re-extracted with ether (2×200 mL). The combined organic layers was washed with saturated brine solution. The organic layer was dried with magnesium sulphate, filtered and concentrated to give a purple solid. The solid was triturated with 5% ethyl acetate in hexanes solution. The grey solid was collected by filtration and air-dried to give 7.59 g of product. ¹HNMR (200 MHz, DMSO-d₆) δ7.96 (1H, d, J=2.37 Hz), 7.71–7.44 (6H, m), 6.56 (1H, d, J=8.98 Hz).

EXAMPLE 8

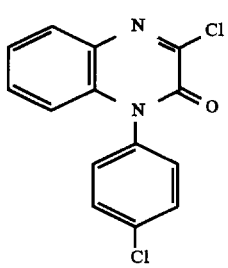

7

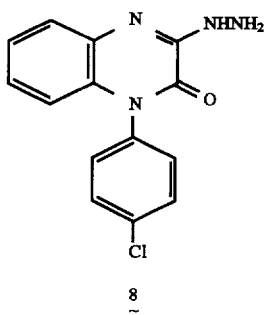

8

To a suspension of the chloroimine 7 (7.38 g, 60.41 mmol) in 75 mL ethanol was added hydrazine (31 mL). The mixture was refluxed for 1 hour. The mixture was cooled to room temperature and diluted with 45 mL of water. The solid was collected by filtration then washed with water (2×60 mL), methanol (1×30 mL) and ether (2×40 mL). The light purple solid was air-dried to give 6.68 g of the hydrazone 8.

¹HNMR (400 MHz, DMSO-d₆) δ9.30 (1H, s), 7.66–7.55 (3H, m), 7.42–7.40 (2H, m), 7.02 (1H, dd, J=8.92, 2.41 Hz), 6.34 (1H, d, J=8.68 Hz), 4.74 (2H, s).

EXAMPLE 9

2-Chloro-acetic acid [4-(4-chloro-phenyl)-3-oxo-3,4-dihydro-1H-quinoxalin-2-ylidene]-hydrazide

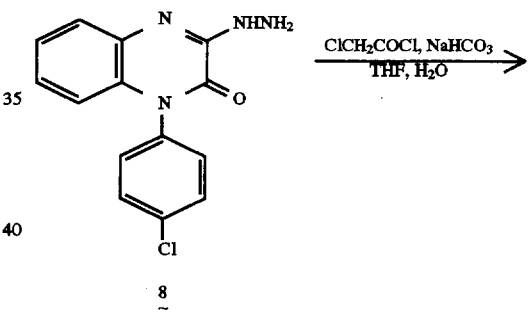

8

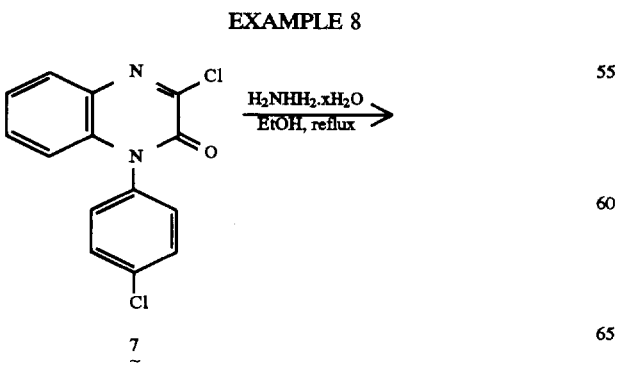

9

To a solution of the hydrazone 8 (3.58 g, 12.49 mmol) in 250 mL of tetrahydrofuran was added 100 mL of half saturated sodium bicarbonate solution. Chloroacetyl chloride (1.5 mL, 18.83 mmol) was added slowly into the reaction mixture at room temperature. The mixture was stirred at room temperature for 30 minutes. Water (100 mL) was added then the mixture was saturated with sodium chloride. The organic layer was collected and the aqueous layer was extracted with ethyl acetate (3×70 mL). The combined organic layers was dried with magnesium sulphate, filtered and concentrated to give a brown solid. The solid was dissolved in 200 mL of hot methanol. Charcoal (2.5 g) was added and the mixture was heated to boiling. The mixture was filtered hot and the filtrate was allowed to cool to room temperature. A white solid was obtained which was collected by filtration and washed with ether (2×60 mL). The solid was air-dried to give 2.88 g of the hydrazide 9; mp=213–214° C.

Anal. Calcd for $C_{16}H_{12}CN_4O_2$: C, 52.91; H, 3.33; N, 15.43. Found: C, 53.14; H, 3.34; N, 15.44.

EXAMPLE 10

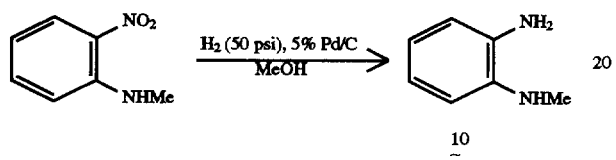

A mixture of N-methyl-o-nitroaniline (16.3 g, 0.107 mol) and 5% Pd/C catalyst (0.6 g) in 100 mL of methanol was shaken in a Parr shaker under 50 psi of hydrogen for 3.5 hours. The catalyst was removed by filtration and the filtrate was concentrated to give a dark oil. The oil was then passed through a column of silica gel eluted with 50% ethyl acetate in hexanes to remove baseline impurities. The diamine 10 was obtained in 13.76 g yield as an orange-colored oil.

$^1$HNMR (300 MHz, CDCl$_3$) δ6.91–6.67 (4H, m), 3.35 (3H, s), 2.88 (3H, s).

EXAMPLE 11

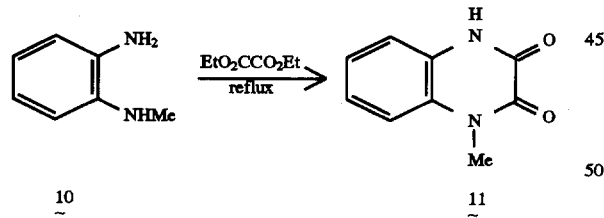

A mixture of the diamine 10 (7.38 g 60.41 mmol) and diethyl oxalate (24 g, 0.164 mol) was refluxed overnight. The blue suspension was cooled to room temperature and then diluted with ethanol (20 mL). The precipitates were collected by filtration and washed with ethanol (2×40 mL). The resulting blue solid was recrystallized in methanol (800 mL) to give 6.76 g of the quinoxalinedione 11 as a grey powder.

$^1$HNMR (300 MHz, DMSO-d$_6$) δ12.02 (1H, s), 7.37–7.33 (1H, m), 7.21–7.16 (3H, m), 3.51 (3H, s).

EXAMPLE 12

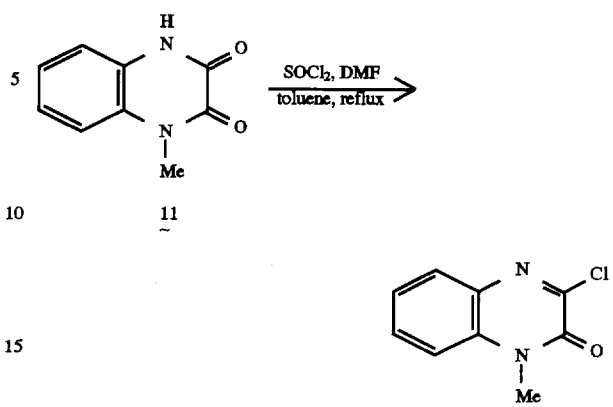

To a suspension of the quinoxalinedione 11 (1.87 g, 10.61 mmol) in 120 mL of anhydrous toluene and 6 mL of anhydrous dimethylformamide was added thionyl chloride (1.2 mL, 16.45 mmol). The reaction mixture was refluxed overnight. The brown solution was cooled to room temperature. Water (50 mL) was added to wash off excess dimethylformamide. The organic layer was collected and dried with magnesium sulphate. The mixture was filtered and concentrated to give 2.1 g of the chloroimine 12 as a brown solid. The material was used without further purifications.

$^1$HNMR (300 MHz, CDCl$_3$) δ7.78–7.30 (4H, m), 3.74 (3H, s).

EXAMPLE 13

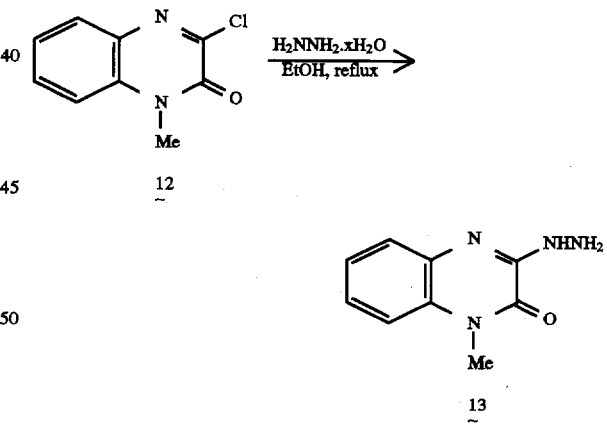

To a suspension of the chloroimine 12 (2.1 g, 10.79 mmol) in 30 mL of ethanol was added hydrazine hydrate (13 mL). The mixture was refluxed for 1 hour then cooled to room temperature and diluted with 20 mL of water. The yellow precipitate was collected by filtration and air-dried. It was then recrystallized in 60 mL of ethanol to give 1.56 g of the hydrazone 13 as off-white needles.

$^1$NMR (300 MHz, CDCl$_3$) δ7.65–7.55 (1H, m), 7.38 (1H, br s), 7.35–7.20 (3H, m), 4.09 (1H, s), 4.08 (1H, s), 3.72 (3H, s).

EXAMPLE 14

2-Chloro-acetic acid (4-methyl-3-oxo-3,4-dihydro-1H-quinoxalin-3-ylidene)-hydrazide

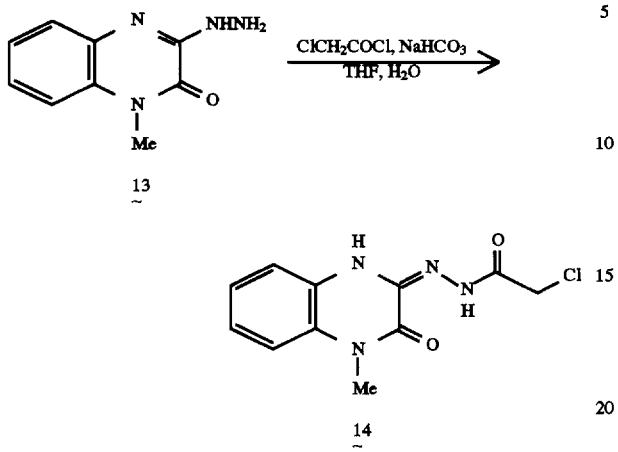

To a solution of the hydrazone 13 (1.13 g, 5.94 mmol) in 60 mL of anhydrous tetrahydrofuran at 0° C. was added chloroacetyl chloride (0.52 mL, 6.53 mmol). The reaction mixture turned into a white suspension immediately. The suspension was stirred at 0° C. for 15 minutes then at room temperature for i hour. Saturated sodium bicarbonate solution (100 mL) was added. The reaction mixture turned into a yellow solution and a white precipitate slowly reappeared on further stirring. The reaction mixture was stirred at room temperature for 15 minutes. The precipitate was collected by filtration. The solid was washed with water (3×60 mL) followed by ether (2×60 mL). The solid was recrystallized in 550 mL of ethanol to give 1.24 g of the hydrazide 14 as a white powder, mp=194°–195° C. (dec). Anal. Calcd for $C_{11}H_{11}ClN_4O_2$: C, 49.54; H, 4.16; N, 20.59. Found: C, 49.40; H, 4.10; N, 20.59.

We claim:

1. A compound of Formula

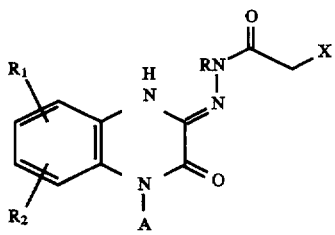

the tautomers or a pharmaceutically acceptable salt thereof wherein

A is alkyl or

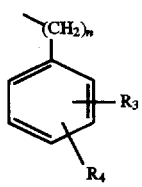

wherein n is an integer of from 0 to 3;

$R_1$ and $R_3$ are each independently
hydrogen,
alkyl,
alkenyl,
alkynyl,
aryl,
arylalkyl,
arylalkenyl, and
arylalkynyl $R_2$ and $R_4$ are each independently
hydrogen,
halogen,
hydroxy,
alkyl,
alkoxy,
nitro,
cyano, and
$COOR_5$ wherein $R_5$ is hydrogen, alkyl, or aryl;

R is hydrogen,
alkyl, or
aryl; and

X is halogen,
alkoxy, or $-O_2CR_6$ wherein $R_6$ is hydrogen, alkyl, or aryl;

alkyl is from 1 to 6 carbon atoms;

aryl is selected from phenyl; biphenyl and naphthyl which are unsubstituted or substituted with from 1 to 3 substituents selected from halogen, nitro, alkyl, alkoxy, alkylthio, and hydroxy.

2. A compound according to claim 1 wherein $R_1$ and $R_3$ are each independently hydrogen;

$R_2$ and $R_4$ are each independently selected from hydrogen, halogen, hydroxy, and $COOR_5$ wherein $R_5$ is hydrogen, alkyl, or aryl;

R is hydrogen or alkyl; and

X is halogen or $-O_2CR_6$ wherein $R_6$ is hydrogen, alkyl, or aryl.

3. A compound according to claim 1 wherein

R, $R_1$, and $R_2$ are each hydrogen;

A is methyl, phenyl, or 4-chlorophenyl; and

X is chloro or bromo.

4. A compound selected from
2-chloro-acetic acid (4-methyl-3-oxo-3,4-dihydro-1H-quinoxalin-2-ylidene)-hydrazide;
2-bromo-acetic acid (3-oxo-4-phenyl-3,4-dihydro-1H-quinoxalin-2-ylidene)-hydrazide;
2-chloro-acetic acid [4-(4-chloro-phenyl)-3-oxo-3,4-dihydro-1H-quinoxalin-2-ylidene]-hydrazide; and
2-chloro-acetic acid (3-oxo-4-phenyl-3,4-dihydro-1H-guinoxalin-2-ylidene)-hydrazide.

5. A pharmaceutical composition comprising a therapeutically effective amount of a compound according to claim 1 together with a pharmaceutically acceptable carrier in unit dosage form.

6. A method of treating ischemia which comprises administering to a mammal in need of such treatment an effective amount of a pharmaceutical composition according to claim 5.

* * * * *